United States Patent [19]

Brethauer

[11] Patent Number: 5,185,003
[45] Date of Patent: Feb. 9, 1993

[54] PORT FOR INJECTING MEDICAMENTS

[75] Inventor: Ullrich Brethauer, Koerle, Fed. Rep. of Germany

[73] Assignee: B. Braun Melsungen AG, Melsungen, Fed. Rep. of Germany

[21] Appl. No.: 833,601

[22] Filed: Feb. 11, 1992

Related U.S. Application Data

[63] Continuation of Ser. No. 497,419, Mar. 22, 1990, abandoned.

[30] Foreign Application Priority Data

Apr. 11, 1989 [DE] Fed. Rep. of Germany ... 8904527[U]

[51] Int. Cl.⁵ .............................................. A61M 11/00
[52] U.S. Cl. .................................... 604/93; 604/175; 604/8
[58] Field of Search ............... 604/190, 93, 175, 86, 604/252, 180, 174, 8, 9, 51

[56] References Cited

U.S. PATENT DOCUMENTS

| | | | |
|---|---|---|---|
| 3,722,697 | 3/1973 | Burke et al. | 604/252 X |
| 3,788,486 | 1/1974 | Bergstrom | 210/496 |
| 4,080,431 | 3/1978 | Moss | 423/289 |
| 4,258,711 | 3/1981 | Tucker et al. | 604/93 X |
| 4,464,178 | 8/1984 | Dalton | 604/174 |
| 4,496,343 | 1/1985 | Prosl et al. | 604/86 |
| 4,605,395 | 8/1986 | Rose et al. | 604/9 |
| 4,781,680 | 11/1988 | Redmond et al. | 604/93 |
| 4,784,646 | 11/1988 | Feingold | 604/175 |
| 4,936,831 | 6/1990 | Jaehrling et al. | 604/131 |
| 5,006,115 | 4/1991 | McDonald | 604/175 |
| 5,013,298 | 5/1991 | Moden et al. | 604/93 |

FOREIGN PATENT DOCUMENTS

| | | | |
|---|---|---|---|
| 0111723 | 6/1984 | European Pat. Off. | 604/86 |
| 0134745 | 3/1985 | European Pat. Off. | 604/175 |
| 3309788 | 10/1984 | Fed. Rep. of Germany . | |
| 3641107 | 6/1987 | Fed. Rep. of Germany . | |
| 3628337 | 2/1988 | Fed. Rep. of Germany . | |

Primary Examiner—C. Fred Rosenbaum
Assistant Examiner—Mark O. Polutta
Attorney, Agent, or Firm—Spensley Horn Jubas & Lubitz

[57] ABSTRACT

A port for injecting medicaments through an implanted catheter. A capsule is formed by a bottom, a circumferential wall defining a cavity and a pierceable upper wall for closing the cavity. The circumferential wall of the capsule has an outlet opening that is shielded by a filter member and to which one end of the catheter is connected. A highly porous filter member of sintered material abuts the cross section of the outlet opening in the circumferential wall. Since the canula tip piercing the upper wall stays clear of the filter member, its position relative to the outlet opening is not influenced by the canula tip and—independent from the material of the sintered filter member—it is not damaged by the canula tip.

16 Claims, 2 Drawing Sheets

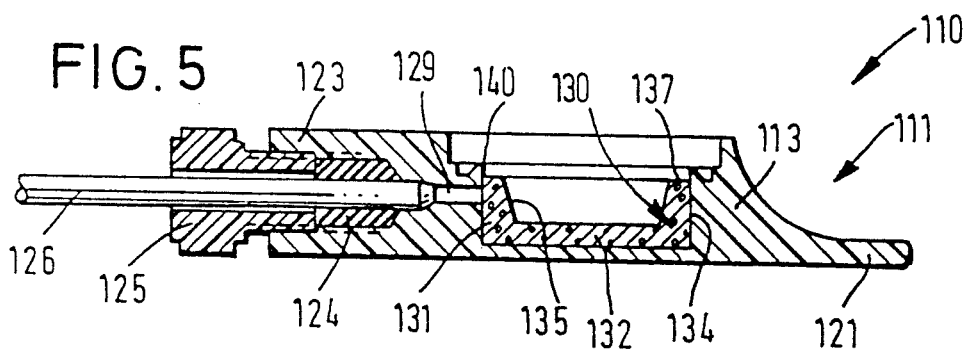
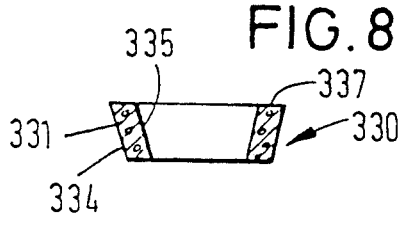
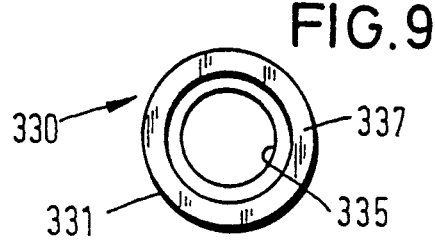
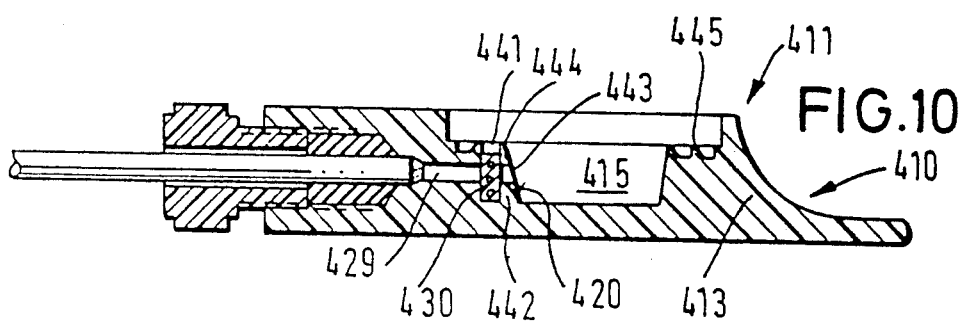
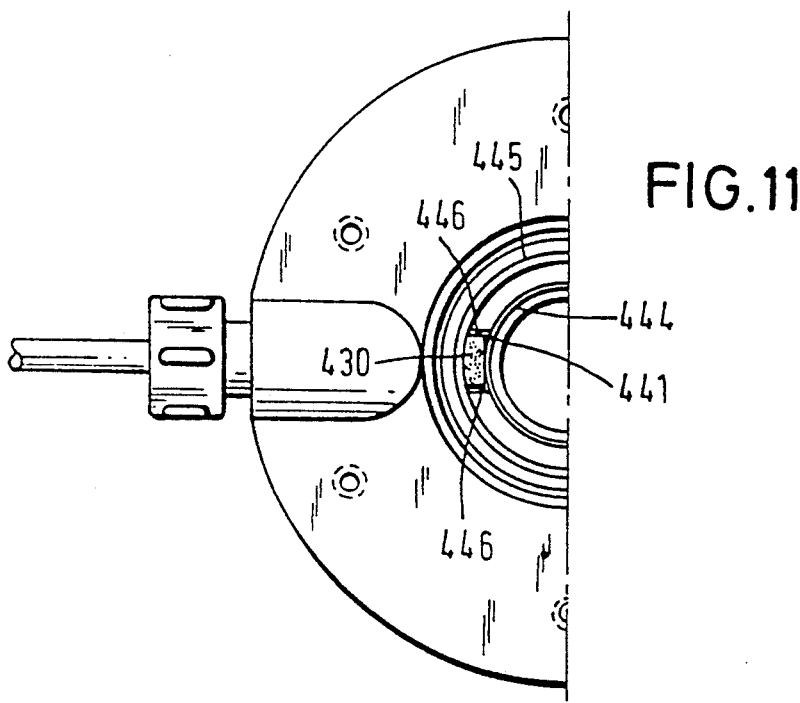

PORT FOR INJECTING MEDICAMENTS

This is a continuation of application Ser. No. 07/497,419 filed on Mar. 22, 1990 now abandoned.

BACKGROUND OF THE INVENTION

1. Field of the Invention

The present invention relates to a port for injecting medicaments through an implanted catheter. More particularly, the present invention relates to a port for injecting medicaments through an implanted catheter consisting of a capsule formed by a bottom, a circumferential wall enclosing a cavity, and a pierceable upper wall closing the cavity, the circumferential wall of the capsule having an outlet opening that is shielded by a filter member and to which one end of the catheter is connected.

2. Description of Related Art.

Such ports, also called "injection members", are known (German Patent 33 09 788) and generally implanted together with the catheter. The capsule has the form of a round flat shell, the cavity of which is tightly sealed by the upper wall consisting of an elastic membrane. The upper edge of the shell is configured such that one may dispose of a maximum elastic membrane surface as the injection surface. In the plane of the bottom, the capsule has a radially projecting annular flange provided with holes for suturing the capsule to the fascia. In the above known port, the outlet opening in the circumferential wall of the capsule is in communication with a radial connecting piece on which the catheter end may be plugged. An improved connection between the port and the catheter is obtained by inserting the catheter into a connecting piece of the capsule and by clamping the same by means of a sleeve-like elastomeric clamping member that may be radially deformed by a pressure member connectable with the connecting piece and which fixedly clamps the catheter (German Patent 36 28 337).

In practical use, it often happens that the pierceable upper wall (port membrane) is not perforated with port canulas specially designed for that range of application, but that users apply conventional cannulas having a disadvantageous thickness and grinding geometry. This results in fine material chips being punched out of the elastomeric upper wall that can clog the outlet opening in the circumferential wall of the capsule or the catheter itself or which may be transferred into the blood vessels. In a subcutaneous injection device according to German Patent 36 41 107, this is to be prevented by means of a porous plug of foamed material that is covered by a metal sieve and arranged above the outlet opening, bridging the cross section of the cavity and extending in parallel to the bottom thereof. This arrangement is not permanently reliable since the plate-shaped plug of foamed material that is held in the cavity of the capsule only at its rim, may loosen due to a repeated pressing of the canula tip on the superimposed metal sieve in the capsule and may thus become leaky at the rim.

It is an object of the present invention to improve a port of the initially mentioned type such that a highly effective filter is entirely functional over long periods of time.

SUMMARY OF THE INVENTION

In accordance with the present invention, this and other objectives are achieved by providing a highly porous filter of sintered material applied to the cross section of the outlet opening in the circumferential wall.

A filter member of sintered material with a pore size of, e.g., 20 $\mu$m has the effect that chips of the elastomeric material chipped off the upper wall with a punching canula are retained at the filter member. Due to the fineness of the filter, the punched out particles are held in the cavity of the capsule as if in a cage and cannot pass through the narrow lumen of the port's outlet opening. The outlet opening is reliably kept open and also the catheter cannot get clogged or transfer chips into the patient's blood circulation. Independent from the number of puncturings of the pierceable upper wall of the capsule, a safe injection through the port is guaranteed, since the filter member is arranged in a vertical plane adjacent the plane of movement of the puncturing canula so that it will not get into contact with the tip of the canula. Since the pressure force of the canula piercing the upper wall never acts on the filter member, its position relative to the outlet opening is not influenced by the canula tip.

Advantageously, the sintered material of the filter member consists of a highly porous stainless steel or of other metal materials, such as nickel, Hastelloy C, B and X, titanium, Monel, Inconel or Incoloy. These and other qualities are employed when iron-based alloys would not be sufficient to provide corrosion resistance. Thus, it may be advantageous in the above mentioned application, particularly in connection with a substance containing hydrochloric acid, to make the highly porous filter member from titanium. Depending on the application, it is advantageous to provide graduations in the fineness of the filter in a range from 0.5 to 200 $\mu$m.

It is a further advantage of making the filter member of a sintered metal that no additional contrast rings to be reproduced on X-ray pictures have to be incorporated in the capsule, since the metal filter member provides an optimum X-ray contrast.

Alternatively, the sintered material may consist of plastic or ceramic material, like glass. In both cases, the highly porous filter member provides a protection of the outlet opening of the port by retaining foreign particles in the cavity and providing unobstructed flow and durability.

In one embodiment of the invention, the filter member is provided as a disc arranged in a pocket of the circumferential wall, the inner wall of which has a bore that is aligned with the outlet opening. The disc of highly porous sintered material is incorporated into the bleed channel and protects it against stopping. However, it cannot be ruled out that the bore in the inner wall of the pocket may become clogged by punched out particles.

A more comprehensive protection is provided by a filter member formed as a ring, the circumferential shape and the height of which are adapted to the cavity of the capsule. The ring may be conical or cylindrical on the outside and/or on the inside. The outer shape depends on the shape of the inner side of the circumferential wall surrounding the cavity, while the inner shape of the ring depends on various practical considerations. A conical inner surface is preferred.

In one advantageous embodiment of the invention, the edge of the ring adjacent the upper wall is provided as a cutting edge penetrating into the upper wall. In this manner, the tightness to the adjacent elastic membrane is improved, so that no particles can get behind the filter below the upper wall. Moreover, the cutting edge provides a firmer press-fitting of the elastomeric upper wall secured to the capsule.

In another preferred embodiment of the invention, one end of the ring is provided with a bottom portion abutting on the bottom of the cavity of the capsule. This is particularly favorable, since the bottom portion of the ring of sintered material protects the bottom of the plastic capsule against perforations that have occurred up to the present when inexpert punctures were made applying too much strength. The bottom portion of sintered metal, integrally formed with the ring, covers the bottom of the cavity of the capsule and protects it so that it can no longer be perforated unintentionally. The reliability of the port is increased, since there are no leakings for the dose of medicament injected into the capsule. A filter member with a bottom portion as a protection against piercing requires a somewhat larger cavity of the capsule, which, however, need not have any effect on the overall height of the capsule to be implanted, because the bottom of the capsule, protected by the bottom portion of the sintered metal ring, may be thinner than before.

BRIEF DESCRIPTION OF THE DRAWINGS

A detailed description of preferred embodiments of the invention will be made with reference to the accompanying drawings.

FIG. 5 shows a cross section of a port with another embodiment of a filter member.

FIGS. 8 and 9 show a cross section and a top plan view of another form of a ring without a bottom, and FIGS. 10 and 11 show a cross section and a top plan view of a port provided with a disc-shaped filter member.

DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
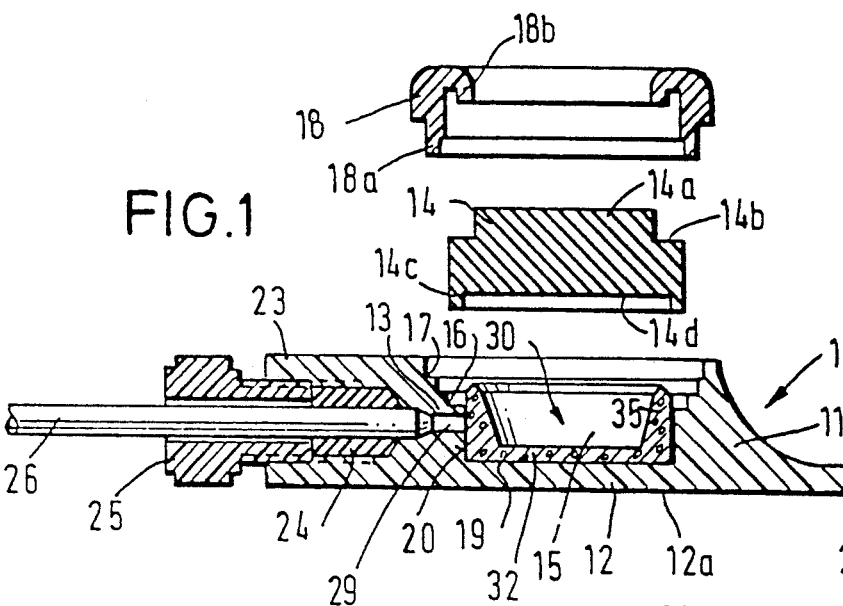
FIG. 1 shows an exploded view of a port with a filter member in cross section.

As illustrated in FIG. 1, the port 10 consists of a capsule 11 which, in top plan view, is circular. The capsule 11 has a bottom 12, a circular circumferential wall 13 and a pierceable upper wall 14 that is provided as a thick elastic membrane of silicon rubber. The bottom 12, the upper wall 14 and the circumferential wall 13 with a circular cylindrical inner side 20 enclose a cavity 15 that can be filled with a liquid medicament by means of a canula pierced through the upper wall 14. The upper wall 14 is provided as a circular profiled disc with a twice stepped cylindrical outer circumference. A central thick portion 14a is surrounded by a radially prolonged stepped ring shoulder 14b. A rim 14c axially projecting from the lower surface 14d forms a support fitted into the lowest recess 16 of the ring having the smallest diameter provided in the inner surface of the circumferential wall 13. A retaining ring 18, projecting with a coaxial projection 18a into the outer-most ring recess 17 having the largest diameter provided in the circumferential wall 13, engages over the ring shoulder 14b of the upper wall 14 with an inwardly bent edge flange 18b and presses the ring shoulder against its seat. The circumferential wall 13 and the retaining ring 18 are bonded or welded together. The edge flange 18b of the retaining ring 18 forms a bead-shaped collar surrounding the central portion 14a of the upper wall 14 and facilitates feeling it through the skin with the port implanted.

Figure 2:
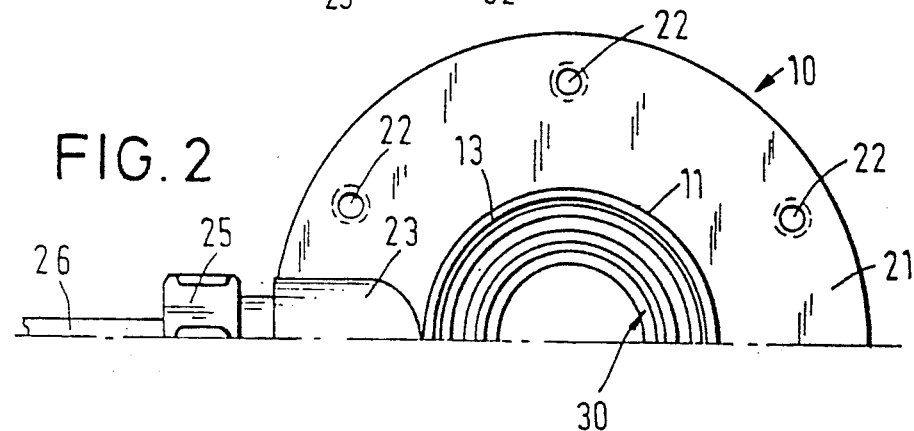
FIG. 2 shows a top plan view of a half of the port without the retainer and the upper wall.

In the plane of the bottom 12, the capsule 11 is formed with a radially projecting annular flange 21 having holes 22 (FIG. 2) for suturing the port 10 to the fascia. The undersurface 12a of the bottom 12 and of the flange 21 form a smooth surface extending in parallel to the plane parallel surface 19 of the bottom 12. A connecting piece 23 projects upward from the flange 21, passing into the circumferential wall 13 of the capsule 11 on the outside. The free end of the connecting piece 23 does not extend beyond the outer edge of the flange 21. The connecting piece 23 has a cylindrical clamping space in which an adapted sleeve-shaped elastomeric clamping member 24 is accommodated, against which the front face of a pressure member 25 presses axially, the pressure member being axially adjustable by virtue of an inner threading in the clamping space and an outer threading at the pressure member 15. Pressure member 25 and clamping member 24 are provided with a coaxial longitudinal channel serving for the passage of a catheter 26 which is clamped in the connecting piece 23 by the radially deforming clamping member 24. The channel in the clamping member 24 and the pressure member 25 is aligned with an outlet opening 29 in the circumferential wall 13 of the capsule 11, which ends on the inner side 20 and connects the cavity 15 with the catheter 26.

Figure 3:
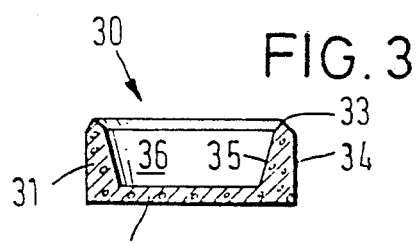
FIGS. 3 and 4 show a cross section and a top plan view of the filter member used in the embodiments of FIGS. 1 and 2.
Figure 4:
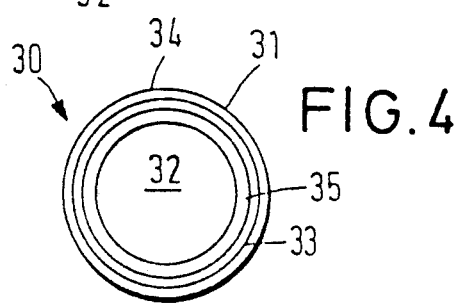
Figure 6:
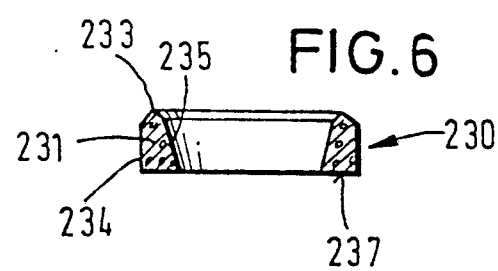
FIGS. 6 and 7 show a cross section and a top plan view of a filter member formed as a ring without a bottom.
Figure 7:
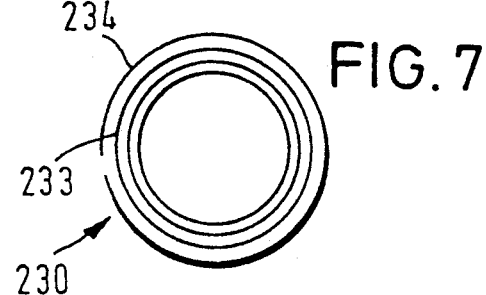

A fitting filter member 30 is inserted into the cavity 15, detailedly illustrated in FIGS. 3 and 4. The filter member 30 consists of a ring 31 of highly porous sintered material, like stainless steel, nickels, titanium or similar suited metallic materials, and its one end is formed with a bottom portion 32 of the same material. The ring 31 of the filter member 30 has a circular cylindrical outer wall 34, the diameter of which is selected such that it is exactly adapted to the diameter of the cavity 15. The inner wall 35 of the ring 31 is conical and tapers towards the bottom portion 32. A cutting edge 33 is formed at the free outer edge of the ring 31, which preferably has a flank angle of 90°. The height of the filter member 30 is such that, when the bottom portion 32 is supported on the inner surface 19 of the bottom 12 of the capsule 11, the cutting edge 33 will penetrate into the underside 14d of the elastomeric upper wall 14 so that the open side of the ring 31 sealingly abuts on the elastic upper wall 14 with a slight pressure, providing it with a firmer press-fitting. Moreover, the cutting edge 33 increases the tightness with respect to the upper wall 14 so that the entire circumference of the cavity 15 between the undersurface 14d of the upper wall 14 and the inner surface 19 of the bottom 12 of the cavity is sealed and particles punched out when perforating the upper wall 14 cannot get to the outlet opening 29. The particles are collected in the cavity of the filter member 30 and clog neither the outlet opening 29 nor the catheter 26.

Besides the separating function, the bottom portion 32 of the filter member 30 is to protect the bottom 12 of the capsule 11 against the penetration of the tip of a canula pushed with too much strength. If the filter member 30 is made of a metal sintered material, the bottom portion 32 forms a support impermeable to the canula tip so that the port bottom 12 cannot be perforated unintentionally.

In the embodiment of FIG. 5, a filter member 130 of suited sintered material that may have a port size of; e.g., 20 μm, is also formed of a ring 131 with a bottom portion 132. The outer wall 134 of the ring 131 is of circular cylindrical shape and the inner wall 135 is conically tapered towards the bottom portion 132. The free edge 137 of this filter member 130 is flat and extends in parallel to the inner surface of the bottom portion 132. The free edge 137 flatly abuts on the lower surface of an elastomeric upper wall pressed by a retaining ring bonded or welded to the circumferential wall 113. A certain degree of sealing the circumference of the filter member 130 against the elastomeric upper wall is obtained by a sharp annular ridge 140 extending coaxially to the cavity at the circumferential wall 113 of the capsule 111 and pressing into the lower surface of the upper wall. An outer radial flange 121 and a connecting piece 123 complement the port 110, as illustrated in FIG. 5. The elements 125, 125 and 126 inserted into the connecting piece 123 are identical to the corresponding elements of the embodiments of FIGS. 1 and 2.

Should the height of the cavity of a capsule 11 or 111 or a port 10 or 110 not be sufficient to provide a ring of a filter member with a bottom portion, one may do without it and obtain the forms illustrated in FIGS. 6 to 9. The filter member 230 is formed as a ring 231 with a circular cylindrical outer wall 234 and a conical inner wall 235, having a cutting edge 233 at its end facing the upper wall of the port, which enters the lower surface of the upper wall, effecting the advantages described in connection with the embodiment of FIGS. 1 and 2. The lower edge 237 of the ring 231 is dull and flat so that it abuts planely on the inner surface 19 of the bottom 12 of the capsule 11.

The embodiment in FIGS. 8 and 9 also illustrates a filter member 330 of highly porous sintered material that consists of a ring 331 open at both ends. The outer wall 334 of this ring 331 and its inner wall 335 are parallel to each other and conical. This filter member 330 fits into a cavity with a conical inner side, the height of which is such that the flat upper edge 337 is firmly pressed against the lower surface of the elastomeric upper wall.

The embodiment of FIGS. 10 and 11 illustrates a general form of configuration of a filter member 430 of highly porous sintered material. This filter member 430 forms a plane-parallel disc only slightly arcuate that is prefixed on the inside to the outlet opening 429 of the circumferential wall 413 of a capsule 411. The disc is positioned in a pocket 441 arranged at the inner end of the outlet opening 429 and delimited over the cavity 415 of the capsule 411 by an inner wall 442 forming the inner side 420 of the cavity 415. In order to prevent a circumferential displacement of the short disc of the filter member 430, the pocket 441 is closed by lateral parts 446. The inner wall 442 has a bore 443 through which liquid medicaments can reach the outlet opening 429 from the cavity 415, the medicament being filtered by the filter member 430 for separating particles chipped off the elastomeric upper wall. The inner wall 442 has its upper edge provided with a sharp annular edge 444 circumferentially extending around the cavity 415 and serving sealing purposes by entering the lower surface of the upper wall. A parallel sharp annular edge 445 on the outer side of the filter member 430 can increase the sealing effect. The remaining elements of the port 410 correspond to the elements described in connection with FIGS. 1 and 2.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A port for injecting medicaments through an implanted catheter, comprising:
    a capsule having a bottom, a circumferential wall and a pierceable upper wall and defining a cavity,
    the circumferential wall having an outlet opening defining a cross section and being adapted for connection with the catheter, and
    a circumferentially shaped porous filter member ring of sintered material applied to and substantially covering the cross section of the outlet opening in the circumferential wall for shielding the outlet opening,
    whereby the filter member lies substantially against the cross section of the outlet opening in the circumferential wall of the capsule.

2. The port as set forth in claim 1, wherein the sintered material is a metallic material.

3. The port as set forth in claim 1, wherein the sintered material is a plastic material.

4. The port as set forth in claim 1, wherein the sintered material is a ceramic material.

5. The port as set forth in claim 2, wherein the sintered material is stainless steel.

6. The port as set forth in claim 2, wherein the sintered material is nickel.

7. The port as set forth in claim 2, wherein the sintered material is titanium.

8. The port as set forth in claim 4, wherein the sintered material is glass.

9. A port for injecting medicaments through an implanted catheter, comprising:
    a capsule having a bottom, a circumferential wall and a pierceable upper wall and defining a cavity,
    the circumferential wall having an outlet opening defining a cross section and being adapted for connection with the catheter, and
    a porous filter member of sintered material applied to and substantially covering the cross section of the outlet opening in the circumferential wall for shielding the outlet opening,
    whereby the filter member lies substantially against the cross section of the outlet opening in the circumferential wall of the capsule,
    wherein the circumferential wall includes a pocket arranged adjacent to the outlet opening and separated from the cavity by an inner wall that forms an inner side of the cavity,
    the inner wall of the pocket defines a bore aligned with the outlet opening through which liquid medicaments can reach the outlet opening from the cavity, and the filter member comprises a disc disposed in the pocket and fixed to the outlet opening of the circumferential wall.

10. A port for injecting medicaments through an implanted catheter, comprising:

a capsule having a bottom, a circumferential wall and a pierceable upper wall and defining a cavity, the circumferential wall having an outlet opening defining a cross section and being adapted for connection with the catheter, and a porous filter member of sintered material applied to and substantially covering the cross section of the outlet opening in the circumferential wall for shielding the outlet opening, whereby the filter member lies substantially against the cross section of the outlet opening in the circumferential wall of the capsule, wherein the filter member comprises a ring having a circumferential shape and a height adapted to conform to the cavity of the capsule.

11. The port as set forth in claim 10, wherein the ring comprises a substantially conical interior surface.

12. The port as set forth in claim 10, wherein the ring comprises a substantially conical exterior surface.

13. The port as set forth in claim 10, wherein the ring comprises a substantially cylindrical interior surface.

14. The port as set forth in claim 10, wherein the ring comprises a substantially cylindrical exterior surface.

15. The port as set forth in claim 10, wherein the ring comprises a bottom portion configured to abut the bottom of the capsule.

16. The port as set forth in claim 10, wherein the ring comprises a cutting edge configured to penetrate into the upper wall.

* * * * *